United States Patent
Denker et al.

(10) Patent No.: US 6,592,518 B2
(45) Date of Patent: Jul. 15, 2003

(54) CARDIAC MONITORING SYSTEM AND METHOD WITH MULTIPLE IMPLANTED TRANSPONDERS

(75) Inventors: Stephen Denker, Mequon, WI (US); Cherik Bulkes, Sussex, WI (US); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 0 days.

(21) Appl. No.: 10/113,198

(22) Filed: Mar. 28, 2002

(65) Prior Publication Data

US 2002/0147405 A1 Oct. 10, 2002

Related U.S. Application Data

(60) Provisional application No. 60/281,819, filed on Apr. 5, 2001.

(51) Int. Cl.[7] .............................. A61B 5/02; A61B 5/00
(52) U.S. Cl. ..................... 600/300; 600/481; 600/507; 600/508; 600/526
(58) Field of Search ................................ 600/300, 504, 600/507, 481, 508, 526

(56) References Cited

U.S. PATENT DOCUMENTS

| | | |
|---|---|---|
| 5,526,772 A | 6/1996 | Curkendall |
| 5,704,352 A | 1/1998 | Tremblay et al. |
| 5,846,200 A | 12/1998 | Schwartz |
| 5,967,986 A | 10/1999 | Cimochowski et al. |
| 6,139,500 A | 10/2000 | Clark |
| 6,208,894 B1 * | 3/2001 | Schulman et al. .............. 607/2 |
| 6,239,724 B1 | 5/2001 | Doron et al. |
| 6,385,482 B1 | 5/2002 | Boksberger et al. |

FOREIGN PATENT DOCUMENTS

| | | |
|---|---|---|
| WO | WO 00/32092 | 6/2000 |
| WO | WO 00/38571 | 7/2000 |

* cited by examiner

*Primary Examiner*—Max F. Hindenburg
*Assistant Examiner*—Navin Natnithithadha
(74) *Attorney, Agent, or Firm*—George E. Haas; Quarles & Brady LLP

(57) ABSTRACT

A plurality of radio frequency semi-passive transponders are attached to an animal's organ, such as the heart. Each semi-passive transponder may be attached to the surface of the organ or mounted on a stent that is implanted in a blood vessel of the organ. An interrogator periodically sends a signal to each semi-passive transponder which reacts by transmitting a reply signal. The interrogator processes the reply signals to derive information regarding activity of the organ. In one embodiment, the position of each semi-passive transponder is determined from the reply signals, thereby enabling information about organ movement and volume change to be derived. In another embodiment, data from a sensor on the semi-passive transponder is sent via the reply signal.

21 Claims, 2 Drawing Sheets

CARDIAC MONITORING SYSTEM AND METHOD WITH MULTIPLE IMPLANTED TRANSPONDERS

CROSS-REFERENCE TO RELATED APPLICATIONS

This application claims benefit of U.S. Provisional Patent Application No. 60/281,819 filed Apr. 5, 2001.

STATEMENT REGARDING FEDERALLY SPONSORED RESEARCH OR DEVELOPMENT

Not Applicable

BACKGROUND OF THE INVENTION

1. Field of the Invention

The present invention relates to devices for monitoring cardiac function in animals, and more particularly to such monitoring apparatus which employ components implanted in the animal.

2. Description of the Related Art

Patients with coronary disease often require monitoring in order to detect changes in their heart function. For example, cardiologists often are interested in cardiac output which is the amount of blood pumped from the heart during each cycle. The cardiac output can be determined from detecting the change in volume as the heart contracts. In other cases, it is desirable to detect movement of various portions of the heart to determine whether the heart muscles are functioning properly.

Most procedures for monitoring cardiac activity and motion employ complex imaging of the heart using ultrasound, radio isotopes or magnetic resonance imaging apparatus and require that the patient go to a facility with the proper imaging equipment.

As a consequence, it is desirable to provide an apparatus which can monitor heart motion without the use of special facilities. There also is a desire to be able to observe blood flow through coronary arteries and monitor cardiac output on a continuous basis.

SUMMARY OF THE INVENTION

An apparatus for monitoring activity of an organ, such as the heart, in an animal comprises a transmitter for wirelessly sending an interrogation signal through the animal. One or more transponders, adapted to be attached to the organ, produce a reaction in response to receipt of the interrogation signal. In the preferred embodiment, that reaction comprises sending a reply signal wirelessly through the animal. A receiver detects the reaction of each transponder and a controller determines a characteristic of the organ based on the reaction of each transponder.

For example, the position of each transponder, and thus the position of that part of the organ at which the transponder is located, can be determined by analyzing the intensity or relative time of receipt of the reply signals. The positions of the respective transponders then can be used to derive the volume of the organ and volume changes over time can be observed as in the case of a beating heart. Sensors also may be connected to the transponders to measure a physical characteristic of the organ and send information about that characteristic via the reply signal.

DETAILED DESCRIPTION OF THE INVENTION

Figure 1:
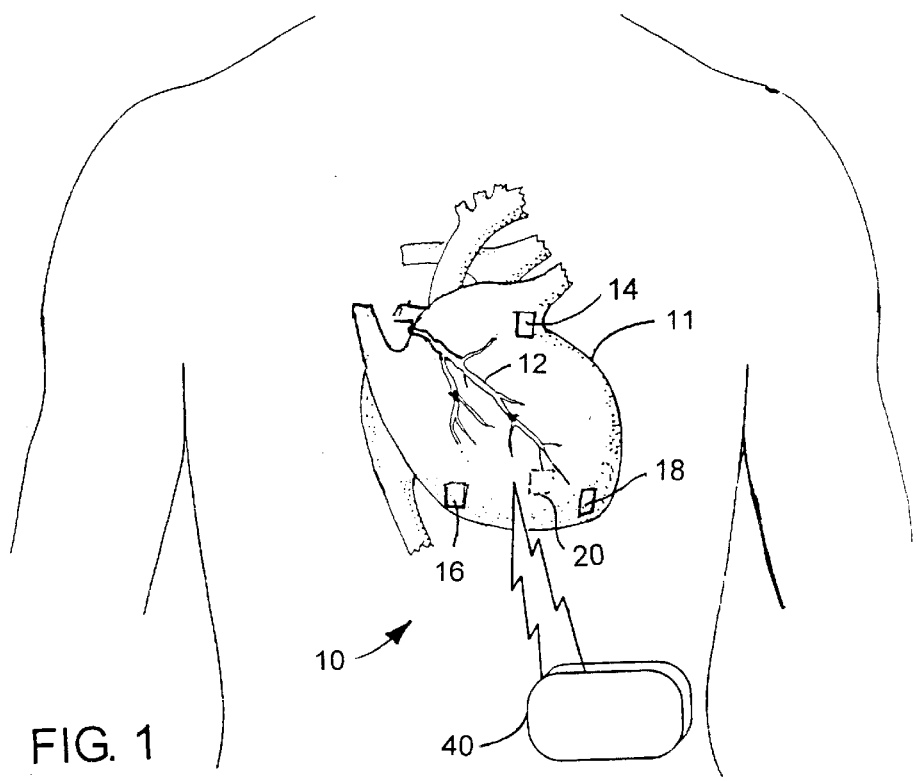
FIG. 1 is a view of components of the present invention implanted in a patient.
Figure 2:
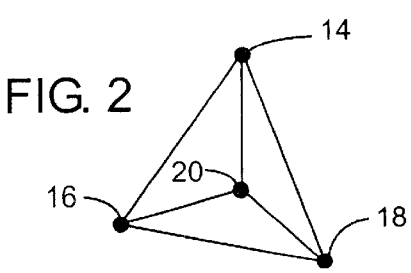
FIG. 2 illustrates the geometric relationship of four transponders used in a system of FIG. 1.

FIG. 1 shows an apparatus 10 for monitoring performance of a heart 11 within a patient wherein the heart has blood vessels 12 which supply blood to the heart muscles. It should be understood that although the present invention is being described in the context of monitoring the heart, it can be used to monitor other organs. A number of radio frequency transponders, for example four, 14, 16, 18 and 20 are attached to the surface of the heart 11 using sutures, adhesive or similar mechanisms. Transponder 20 is located on the rear surface of the heart. As seen in FIG. 2, the four transponders 14–20 are not located in the same plane and thus their positions can be represented as the apexes of a tetrahedron. Additional transponders can be placed on the heart, in which case a polyhedron with more apexes would be formed. The transponders 14–20 move with the exterior surface as the heart beats and the size of the tetrahedron changes with changes in the heart size.

Figure 4:
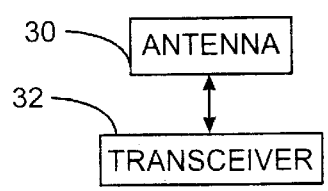
FIG. 4 is a block schematic diagram of a transponder.

Referring to FIG. 4, the circuitry for the transponders 14, 16, 18 and 20 is mounted on a flexible substrate that has conductors interconnecting the circuit components. The four transponders 14, 16, 18 and 20 are semi-passive devices, which as used herein means that the transponders do not have an internal power source, such as a battery, and instead are powered by energy of a radio frequency interrogation signal received by the transponder. Each semi-passive transponder 14–20 contains an antenna 30 which is connected to a radio frequency transceiver 32. The transponders 14–20 are tuned to different frequencies, thereby enabling each one to be accessed independently. Upon receiving a signal at the proper radio frequency, the transceiver 32 transfers the radio frequency signal back to the antenna 30. In this embodiment, the semi-passive transponder merely reflects the received signal and does not convert it either in terms of frequency or content. However, in an alternative embodiment, the transceiver 32 may modify the frequency and/or amplitude envelope so that the reflected signal contains additional spectral or amplitude information than that of the original received signal.

The semi-passive transponders 14–20 are accessed periodically by an interrogator 40. The interrogator 40 preferably is implanted inside the patient, but may be outside the patient and held stationary during the examination process. Implantation of the interrogator is preferred as the location of the interrogator relative to the transponders is important for measuring certain cardiac parameters and variation of that position could adversely affect the ability to compare measurements taken over time.

Figure 5:
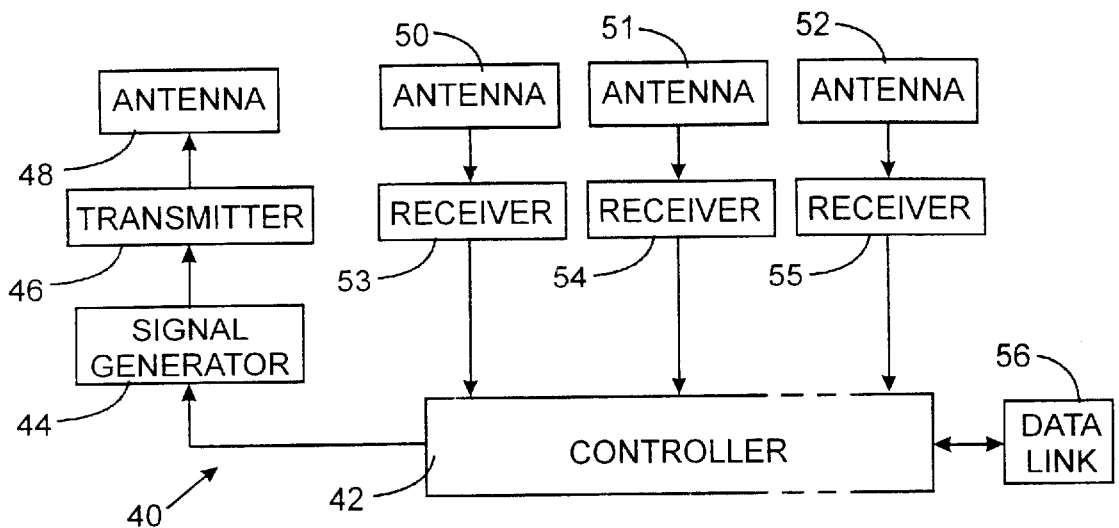
FIG. 5 is a block diagram of an electronic apparatus for interrogating the transponders.

FIG. 5 shows the circuitry of a typical interrogator 40 which has a controller 42 which determines when to interrogate the transponders 14–20 and processes the information from such interrogation. When interrogation is desired, the controller 42 sends a command to a signal generator 44 which instructs a transmitter 46 to select one of the frequencies to which a transponder is tuned. The signal generator 44 also generates a sequence of pulses that cause the transmitter 46 to emit bursts of the selected radio frequency signal. The output of the transmitter 46 is sent to an antenna 48 which emits the signal into the chest of the patient.

Referring again to FIG. 4, if a particular semi-passive transponder 14–20 is tuned to the frequency of the signal sent from the interrogator 40, that transponder's transceiver 32 will echo a reply signal via antenna 36. Upon being excited by the received signal, the respective semi-passive transponder produces a decaying signal, including potential, frequency and amplitude modification, from self resonance to that transponder after the interrogator's transmitted signal ceases, such that the reflected signal does not overlap that signal sent from the interrogator.

The interrogator 40 in FIG. 5 has one broadband or, for example, three narrow band antennas 50, 51 and 52 positioned at different locations with respect to the patient's heart for receiving the transponder reply signals. Each antenna 50, 51 and 52 is connected to a separate receiver 53, 54, or 55 respectively which at this time are all tuned the frequency at which the interrogator had just transmitted a signal. Each receiver 53–55 responds to signals in a band of frequencies centered about that tuned frequency so that reply signals with minor frequency shifts still will be detected. Alternatively a broadband receiver covering all frequency bands including potential frequency shifts may be employed. The intensity and exact frequency of the received reply signal are determined by each receiver 53–55 and that information is fed to the controller 42 for initial storage.

The intensity of the echoed reply signal varies as beating heart causes a transponder 14–20 to move with respect to the antennas of the interrogator 40. Specifically the signal intensity varies with the distance between the transponder and those antennas. Thus changes in the intensity indicate relative movement of the transponder. Alternatively, the time delay between the transmission of the original signal burst from the interrogator 40 and receipt of the reply signal at each receive antenna 50–52 can be used as an indication of the distance between that transponder and the interrogator 40. By knowing the distance between the transponder 14–20 and each receiver antenna 50–52, triangulation can be employed to determine the position of the transponder and thus that part of the heart to which the transponder is attached.

The interrogator 40 sequentially addresses each transponder 14–20 by emitting interrogation signals of the corresponding frequencies. At the same time, the tuning of the receivers 53–55 in the interrogator is changed to the new transmission frequency. In this manner, the interrogator 40 acquires information about the intensity and frequency shift of each reply signal echoed by the respective transponders.

Depending upon the sophistication of the controller 42, the transponder signal information merely may be stored in a memory for downloading to an external computer for evaluation, or the controller 42 may be programmed to evaluate the data internally. In either case, a data link 54 is provided to transfer either the raw data or the data processing results to an external device. For example, if the interrogator 40 is implanted in the patient, the data link 54 can be a coil implanted immediately under the skin of the patient. That coil can be electromagnetically coupled to an external coil to exchange data between the implanted interrogator 40 and an external computer (not shown) using communication techniques similar to those employed to exchange data with an implanted heart pacing device.

Figure 3:
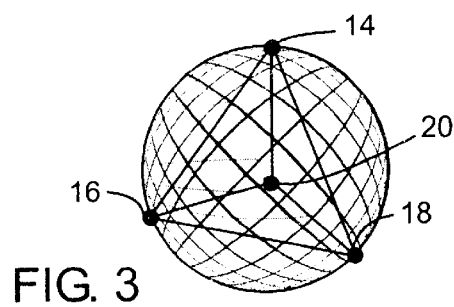
FIG. 3 graphically depicts computation of heart volume employing positions of the transponders.

A sophisticated interrogator 40 is able to determine the relative change in the position of the transponders 14–20 from the change in their signal intensities. Specifically, as the transponder moves closer to a receive antenna 50–52 of the interrogator 40, the intensity of that transponder signal will increase. Conversely when the transponder is moving away from the receive antenna 50–52, the intensity of the reply signal decreases. Therefore, the controller 42 is able to determine the position of each transponder and from that position information determine the size of the tetrahedron formed by the four transponders 14–20 as shown in FIG. 2. The heart 11 can be modeled as a sphere 22 with the four transponders 14–20 located on the surface of that sphere, as shown in FIG. 3, and the volume of the sphere can be determined by the controller 42.

Change in the size of the sphere from one interrogation cycle to the next corresponds to the change in the volume of the portion of the heart included within the volume of the tetrahedron, which then can be used to determine cardiac function. The relative motion of each of the transponders also indicates whether all portions of the heart muscle are functioning properly.

More complex analysis of the transponder signals can be preformed. The motion of a transponder is characterized by both velocity and direction and thus can be represented mathematically as a vector with a length and direction. Thus, the motion of the set of four transponders 14–20 can be expressed as a set of vectors, with a set being created each time the four transponders are interrogated. Motion of the included heart volume can be quantified in the form of mappings or correspondence from one set of these vectors to another, thus forming a tensor. This tensor is a characterization of the heart activity.

Figure 6:
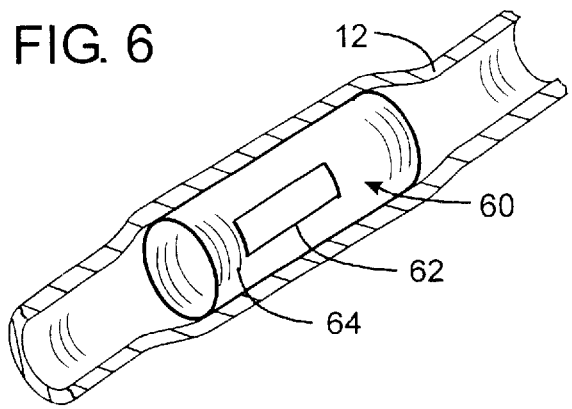
FIG. 6 illustrates an alternative embodiment for a transponder attached to a stent that is placed within a blood vessel.

With reference to FIG. 6, alternatively a semi-passive transponder 60 can be formed by placing its circuitry 62 onto the surface of a vascular stent 64. Such stents are commonly used to enlarge narrowed blood vessels to improve the fluid flow. The stent is an expandable device which is placed in collapsed form around a balloon catheter that then is threaded through the blood vessels typically into an artery of the heart. Once properly positioned, the balloon of the catheter is inflated which also enlarges the stent against the walls of the blood vessel thereby firmly implanting the transponder 60 at that location in the blood vessel.

Although the circuit 62 of the semi-passive transponder 60 on the stent 64 can merely reflect the radio frequency signal back to the interrogator 40 as described previously, the stent transponder also can sense physiological parameters of the patient and modify the reflected signal in response to that sensing. In this manner, data about the patient's physiology are sent to the interrogator 40 which utilizes that information to analyze cardiac performance. For example, the sensors may detect characteristics related to the blood flow or electrical signals produced in the heart. That sensed physiological information then modifies one or more electrical parameters of the transponder, such as by varying a resistor, capacitor or inductor, which alters characteristics of the reflected radio frequency signal to encode the sensed information.

Figure 7:
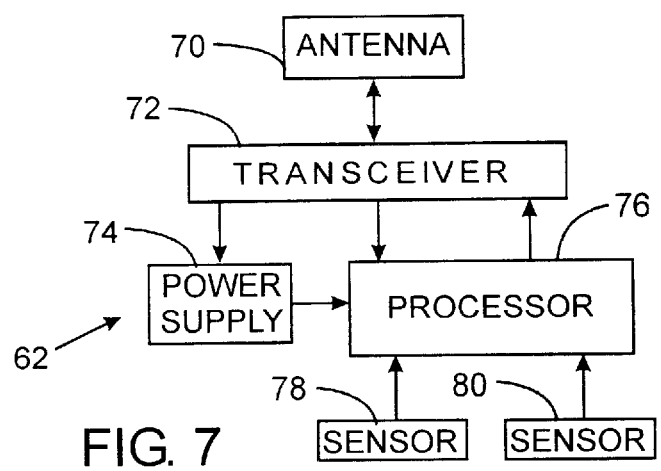
FIG. 7 is a schematic block diagram of the circuitry for the transponder in FIG. 6.

FIG. 7 illustrates more complex sensing circuitry for a stent integrated transponder 62. That transponder has a receiving antenna 70 connected to a transceiver 72 which is tuned to a particular frequency designated for this transponder. The received radio frequency signal provides energy for powering the semi-passive transponder 62 as is typically done with many types of transponders for other applications, such as for unlocking doors of a building. Thus, part of the electrical energy received by the transceiver 72 is diverted to a power supply 74 which provides energy for powering a signal processor 76 within the stent. Upon being powered, the processor 76 reads information from one or more sensors 78 and 80. For example, the sensors 78 and 80 may measure pressure in the blood vessel at opposite ends of the stent 64. These measurements denote a pressure drop across the stent, and thus provide an indication when the stent is closing.

A common problem with stents is that material begins to form inside the stent, thereby reducing the blood flow there through. Such narrowing of the stent can be detected by sensing the pressure drop across the stent which increases as the blood flow is restricted. Thus too great a pressure drop provides an indication to medical personnel that the stent needs to be replaced or cleaned out.

In addition, the absolute pressure in the blood vessel 12 at the stent 64 is useful information regarding the adequacy of blood flow to that location in the heart. Other types of sensors can be connected to the processor 76 to determine the relative flow of blood through the vein, the temperature of that portion of the heart, and other physical characteristics.

The processor 76 obtains and sends the sensor data to a transmitter section of the transceiver 72 which modulates a radio frequency carrier with that sensor information. The frequency of the carrier emitted by transceiver 72 preferably has the same frequency as the signal received from the interrogator 40. The resultant modulated radio frequency signal is transmitted by antenna 70 back to the interrogator 40. In this version where sensor data is modulated on the reply signal from the transponders, the interrogator 40 recovers that modulated data for storage and subsequent analysis. The data also may be provided for processing by computer external to the patient's body via the data link 54 of the interrogator.

The stent 64 follows movement of the containing vessel as the heart beats. The forces exerted on the blood vessel 12 and the flow of fluid through the vessel cause a distortion of the stent which in turn varies the characteristics of the antennas 70 and 84. This results in a corresponding change in the frequency of the reply signal. As a consequence, the distortion of the stent as represented by the frequency change can be employed to indicate forces acting at that point in the heart The foregoing description was primarily directed to a preferred embodiment of the invention. Although some attention was given to various alternatives within the scope of the invention, it is anticipated that one skilled in the art will likely realize alternatives that are now apparent from disclosure of embodiments of the invention. For-example, although the present invention was described in the context of radio frequency signals being used, other types of signals could be employed. Furthermore, reaction of a transponder to receiving an interrogation signal may be other then by transmitting a reply signal. Accordingly, the scope of the invention should be determined from the following claims and not limited by the above disclosure.

What is claimed is:

1. An apparatus for monitoring a physiological characteristic of an internal organ in an animal, that apparatus comprising:
    a plurality of transponders adapted to be attached to the internal organ of the animal and producing a reaction in response to receipt of an interrogation signal that is transmitted wirelessly through the animal;
    a transmitter for transmitting the interrogation signal wirelessly through the animal to each of the plurality of transponders;
    a receiver for detecting a reaction of each transponder to the interrogation signal; and
    a controller which determines the physiological characteristic of the internal organ in response to the reaction detected for each transponder.

2. The apparatus as recited in claim 1 wherein the plurality of transponders are attached to the internal organ in a non-planar array.

3. The apparatus as recited in claim 2 wherein the controller processes the reaction of each of the plurality of transponders to determine a position of each transponder within the animal.

4. The apparatus as recited in claim 3 the controller derives a value for the volume of the internal organ from the position of each transponder.

5. The apparatus as recited in claim 4 wherein the controller determines cardiac output from changes in the volume of the internal organ.

6. The apparatus as recited in claim 1 wherein the reaction of each transponder in response to the interrogation signal comprises transmitting a reply signal wirelessly through the animal.

7. The apparatus as recited in claim 6 wherein the controller determines a position of each transponder in response to an intensity of the reply signal from each transponder.

8. The apparatus as recited in claim 6 wherein the at least one transponder has sensors for detecting the physiological characteristic and transmits information regarding the physiological characteristic via the reply signal.

9. The apparatus as recited in claim 1 wherein each transponder is formed on a stent adapted to be implanted in a blood vessel of the animal.

10. An apparatus for monitoring activity of a heart in an animal, that apparatus comprising:
    a transmitter which transmits a plurality of interrogation signals wirelessly through the animal;
    a plurality of transponders adapted to be attached to the heart and each transponder being responsive to a unique one of the interrogation signals by transmitting a reply signal wirelessly through the animal;
    a receiver for detecting the reply signal from each of the plurality of transponders; and
    a controller which determines positions of the plurality of transponders in response to the reply signals and from those positions produces a value indicating cardiac performance.

11. The apparatus as recited in claim 10 wherein each transponder is formed on a stent adapted to be implanted in a blood vessel of the heart.

12. The apparatus as recited in claim 10 wherein the controller determines movement of the heart from changes in positions of the plurality of transponders.

13. The apparatus as recited in claim 10 wherein the controller derives a value for the volume of the heart from the positions of the plurality of transponders.

14. The apparatus as recited in claim 13 wherein the controller determines cardiac output from changes in the volume of the heart.

15. The apparatus as recited in claim 10 wherein at least one of the plurality of transponders has a sensor that detects a physical characteristic of the animal and transmits information regarding the physical characteristic via the reply signal.

16. The apparatus as recited in claim 15 wherein the at least one of the plurality of transponders is formed on a stent adapted to be implanted in a blood vessel and the sensor provides information regarding a pressure drop across the stent.

17. The apparatus as recited in claim 15 wherein the sensor provides information regarding electrical activity of the heart.

18. A method for monitoring activity of an organ in an animal, that method comprising:

attaching at least one transponder to the organ;

interrogating the transponder with a wirelessly transmitted interrogation signal;

the transponder reacting to the interrogation signal by wirelessly transmitting a reply signal;

receiving the reply signal from the transponder; and processing the reply signal to derive information regarding the activity of the organ.

19. The apparatus as recited in claim 18 wherein processing the reply signal derives information regarding movement of the organ.

20. The apparatus as recited in claim 18 wherein processing the reply signal derives information regarding changes in volume of the organ.

21. The apparatus as recited in claim 18 further comprising sensing a physical characteristic of the organ; transmitting information about that physical characteristic with the reply signal; and wherein processing the reply signal obtain the information about that physical characteristic.

* * * * *